United States Patent [19]

Walters et al.

[11] 4,220,801
[45] Sep. 2, 1980

[54] PROCESS FOR MAKING 4-AROYL-SUBSTITUTED PHENOXYACETIC ACIDS

[75] Inventors: Roland L. Walters, Des Plaines; Wayne R. Heitmann, Park City, both of Ill.

[73] Assignee: Abbott Laboratories, North Chicago, Ill.

[21] Appl. No.: 59,823

[22] Filed: Jul. 23, 1979

[51] Int. Cl.$^2$ ............................................. C07C 69/76
[52] U.S. Cl. ....................................... 562/468; 560/52
[58] Field of Search ........................... 562/468; 560/52

[56] References Cited

U.S. PATENT DOCUMENTS

| 4,058,559 | 11/1977 | Jones et al. | 260/520 C |
| 4,069,344 | 1/1978 | Karrer | 424/324 |
| 4,072,705 | 2/1978 | Mieville | 424/308 |

Primary Examiner—Paul J. Killos
Attorney, Agent, or Firm—Paul D. Burgauer; Robert L. Niblack

[57] ABSTRACT

2,3-Dichloro-4-(hydroxybenzoyl)phenoxyacetic acid, its analogs and their salts are powerful uricosuric diuretics; they can be made in a one-pot reaction from a loweralkyl 2,3-dichloro-4-(nitrobenzoyl)phenoxyacetate or its analogs.

13 Claims, No Drawings

PROCESS FOR MAKING 4-AROYL-SUBSTITUTED PHENOXYACETIC ACIDS

DETAILED DESCRIPTION OF THE INVENTION

From U.S. Pat. No. 4,058,559 it is known that compounds such as 2,3-dichloro-4-(hydroxybenzoyl)-phenoxyacetic acid, its analogs and their salts are antihypertensive agents and diuretics with uricosuric activites. The present invention is concerned with a particularly economical method for preparing those compounds, which carry a hydroxy group in the aroyl moiety.

The current process is thus directed to the manufacture of a compound of the formula

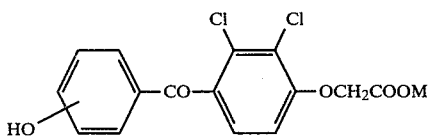

I wherein M is hydrogen, an alkali or half of an alkali earth metal cation, and the HO-group is in the p- or o-positions, consisting essentially in treating an ester of the formula

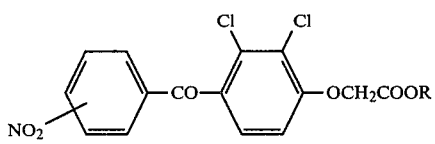

II wherein R is a loweralkyl or a phenyl group, and the $NO_2$—group is in the p- or o-positions with 1.5-8 molar equivalents of an oxime of the formula R'R''—C=NOM' wherein R' and R'' individually are hydrogen, phenyl or loweralkyl and M' is an alkali or half of an alkali earth metal cation, in the presence of DMF or DMSO at a reaction temperature of −10° to 130° C. for a period of at least 30 minutes. The term "loweralkyl" herein is used to identify alkyl groups of 1-4 carbon atoms, preferably methyl and ethyl. The term "phenyl" should be understood herein as referring to phenyl per se or a phenyl group carrying an inert substituent, e.g., methyl, ethoxy, etc. However, the choice of R' as alkyl is preferred as the reaction proceeds faster than in the case where R' is phenyl or substituted phenyl. The alkali and alkali earth metals referred to above are primarily those that are useful in pharmaceutical preparations, i.e., sodium, potassium, calcium and magnesium, although others, such as barium or lithium are also included as they lead to salts that can be converted to the pharmaceutically preferred salts.

The new reaction is best carried out with agitation by suitable means such as mechanical or magnetic stirring, shaking or vibrating the reaction vessel, etc. While the reaction can be carried out in less than one hour, the exothermic reaction is best controlled by agitating the reactants first for 5-10 minutes at a temperature at or below 5° C. and, subsequently, allowing the mixture to attain room temperature with stirring to continue for a total of about 2-15 hours.

When M in the above oxime is hydrogen, the reaction requires longer for completion and one preferably uses a larger molecular excess of the oxime, i.e., 4-8 moles. However, an oxime per se can be used, but a base such as sodium or potassium hydride, alkoxide, carbonate, bicarbonate or hydroxide must be used therewith, forming the oxime salt in situ. Molar amounts of more than 8 moles of oxime+base per mole of the above ester of formula II are permissible but no advantage is gained thereby. Optimum results are obtained by using 3-5 moles of the oxime per mole of II, of course, in the presence of the equivalent amount of base.

The reaction can be carried out equally well in DMF (dimethylformamide) or DMSO (dimethylsulfoxide). Both solvents will dissolve the above reactants and neither is a solvent for the reaction product. The formed di-salt of Compound I will precipitate during the reaction and can easily be separated from the medium by centrifugation or filtration with or without prior concentration of the reaction mixture. The amount of solvent used for the reaction is preferably chosen in such a way that the concentration of II in said solvent lies between 2.5 and 35% wt/vol. At concentrations below 2.5%, the reaction requires an impractically long time to be completed while at concentrations above 25%, the mixture becomes too hard to agitate.

Since the potassium salt of I is of particular interest as an uricosuric diuretic, the oxime used is preferably the potassium salt of a loweralkyl oxime, e.g., acetaldoxime, acetoxime or propionyl aldoxime. While other esters II can be used, preference is given to the more readily accessible methyl, ethyl and propyl esters.

The reaction is best initiated at temperatures below 5° C., although room temperature is perfectly satisfactory except for the initial heat generated by the reaction. To avoid overheating, the reaction may best be initiated at a temperature in the range from −10° to +10° C. In that case, the mixture is then stirred without external cooling so that room temperature will be attained gradually. This can, of course, be accelerated by placing the reaction vessel in a warming bath or heating mantle. The reaction can be completed by continuing the stirring for at least 30 minutes, preferably about 3 hours at 15°–50° C. when R' is alkyl and R''=H or 10-20 hours when either R' or R'' is aryl. The progress of the reaction can be followed by sampling for additional precipitation as the product is insoluble in DMF or DMSO while both reactants are soluble. Temperatures of up to 50° C. or even higher may be used to speed up the reaction, but since with 2-4 molar equivalents of an oxime salt the reaction progresses at a satisfactory rate at 15°–25° C. or room temperature, no need is seen to provide for a heat source.

To better describe the new process, reference is made to the following examples which, however, are illustrations only and are not intended to limit the scope of this invention.

EXAMPLE 1

In a 50 ml. round-bottom flask equipped with a magnetic stirrer, 1.9 g. of potassium acetaldoxime in 12 ml. of DMF is stirred under a $N_2$-blanket while cooling the solution to 0°. After adding 2.0 g. of ethyl 2,3-dichloro-4-(4-nitrobenzoyl)phenoxyacetate, the mixture becomes very dark. The ice-bath is removed after 5 minutes to allow the mixture to attain room temperature. After stirring for a full two hours, the mixture is filtered and the solid is washed with 20 ml. of ether, leaving an almost pure dipotassium salt of I. This material is crystallized by steam-bath heating of a solution thereof in 15 ml. of water, adding sufficient glacial acetic acid to achieve a pH of 4.5–5.0, and allowing the yellow solution to cool slowly to room temperature and then in an ice-bath for one hour. The cold slurry is then filtered and the obtained 0.838 g. of pure crystals of potassium 2,3-dichloro-4-(4-hydroxybenzoyl)phenoxyacetate are dried under reduced pressure at 70° C. Additional product can be obtained from the DMF filtrate by evaporating part of the solvent and proceeding as described, or by adding a non-polar solvent to said filtrate.

When in the above example the defined p-nitrobenzoyl starting material is replaced by the corresponding o-nitro derivatives, a similar yield of potassium 2,3-dichloro-4-2-hydroxybenzoyl)phenoxyacetate is obtained. Similarly, the above used ester can be replaced by the corresponding methyl (substituted) acetate, producing essentially identical results as shown above.

Essentially identical results are also obtained when DMSO replaces the above DMF as the reaction medium.

EXAMPLE 2

In the above described equipment, 0.312 g. of sodium hydride in 17.5 ml. of DMF is stirred while dropwise adding 0.874 ml. of benzaldoxime. The exothermic reaction forms a heavy precipitate while generating hydrogen gas. When the $H_2$-evolution ceases, 1,4806 g. of 2,3-dichloro-4-(4-nitrobenzoyl)phenoxyacetic acid is added, which will start $H_2$-evolution again and produce a homogenous dark solution. Upon further stirring, a precipitate starts to form which after several hours may become heavy enough to interfere with the magnetic stirrer. After 15 hours, the mixture is diluted with 175 ml. of water and filtered. By acidifying the filtrate with concentrated HCl to a pH of 2, a milky oil separates which solidifies upon standing. After collecting the crystalline material by filtration, washing it with cold water and drying it at 60° C. under house vaccum, 1.1986 g. (88% of theory) of 2,3-dichloro-4-(4-hydroxybenzoyl)phenoxyacetic acid is obtained.

EXAMPLE 3

In a 100 ml. round-bottom flask equipped with magnetic stirrer, condenser and heating mantle, is stirred 10.0 g. of ethyl 2,3-dichloro-4-(4-nitrobenzoyl)phenoxyacetate, 5.5 g. of acetoxime, 2.0 g. of sodium hydroxide and 75 ml. of DMF. The slurry is heated for 18 hours at 75°±5° C. then at 125°±5° C. for 4 hours to decompose the oxime adduct. The reaction is poured into 300 ml. of water and acidified to a pH of 1. The product is filtered and dried to yield 8.0 g. of crude 2,3-dichloro-4-(4-hydroxybenzoyl)phenoxyacetic acid. It is identified by thin-layer chromatography as being identical to the product of Example 2.

The above illustrations show that the new process reduces the previous three-step procedure to a single operation. In the case of I where M=H, the pure material can be isolated from the reaction mixture by diluting it with water, and subsequent acidification thereof with a strong acid. If desired, the aqueous solution may be treated with charcoal to eliminate any discoloration. In any event, it may be advisable to filter the solution before acidifying it. Any strong acid may be used for the latter step with hydrochloric or sulfuric acid being particularly economical. When M in formula I is sodium, potassium or ½-calcium, the aqueous solution is acidified only to a pH of 4.5–5.0 to assure that the desired salt is obtained. Here again, the aqueous solution is preferably first filtered and/or treated with charcoal.

As mentioned in Example 1, an intermediate disalt forms, i.e., the salt of I wherein M and the hydrogen of the hydroxy group are represented by the same cation. This salt can easily be isolated by adding either toluene or other non-polar, aprotic solvents to the DMF or DMSO mixture containing it or it can be dissolved by adding water to said mixture.

The starting materials used in the present process can be obtained easily by a Friedel-Crafts reaction from a nitrobenzoyl chloride and 2,3-dichloroanisol, and converting the obtained 2,3-dichloro-4-(nitrobenzoyl)-phenol with ethyl chloroacetate to the desired substituted acetic acid derivative shown in II.

We claim:
1. The process of manufacturing a compound of the formula

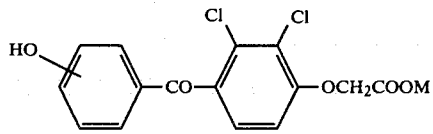

wherein M is hydrogen, an alkali or half of an alkali earth metal cation and said HO-group is in the p- or o-position, consisting essentially in treating an ester of the formula

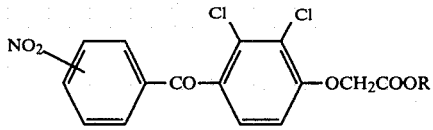

wherein R is a loweralkyl or a phenyl group and the $NO_2$-group is in the p- or o-position, with 1.5–8 molar equivalents of an oxime of the formula R'R"C=NOM' wherein R' and R" individually are hydrogen, phenyl or loweralkyl and M' is an alkali or half an alkali earth metal cation, in the presence of DMF or DMSO at a reaction temperature of −10° to +130° C. for a period of at least 30 minutes.

2. The process of claim 1 wherein said reaction is carried out at temperatures of 0°–5° C. for 5–10 minutes and subsequently at 15°–25° C. for 2 hours, and R' is loweralkyl.

3. The process of claim 1 wherein M' is sodium.

4. The process of claim 1 wherein M' is potassium.

5. The process of claim 1 wherein said oxime is used at a range of 3–5 molar equivalents.

6. The process of claim 5 wherein said DMF or DMSO is used in such an amount that the wt/vol. concentration of said ester is between 2.5 and 35%.

7. The process of claim 6 using DMF as the reaction medium.

8. The process of claim 1 wherein said nitro group is in the p-position.

9. The process of manufacturing potassium 2,3-dichloro-4-(4-hydroxybenzoyl)phenoxyacetate consisting essentially in agitating a solution of 2.5–35% by weight of a loweralkyl ester of 2,3-dichloro-4-(4-nitrobenzoyl)phenoxyacetate in DMF or DMSO with 1.5–8 molar equivalents of a potassium oxime for at least one hour at room temperature and removing the insoluble potassium 2,3-dichloro-4-(4-hydroxybenzoyl)-phenoxyacetate from the liquid reaction medium.

10. The process of claim 9 wherein said oxime is used in an amount of 3-5 moles per mole of said loweralkyl ester.

11. The process of claim 10 wherein said oxime is acetaldoxime.

12. The process of claim 10 wherein said oxime is acetoxime.

13. The process of claim 10 wherein said ester is the methyl ester.

* * * * *